US00PP08999P

United States Patent [19]

Yensen

[11] Patent Number: Plant 8,999

[45] Date of Patent: Nov. 29, 1994

[54] *DISTICHLIS SPICATA* VAR. YENSEN 4A

[75] Inventor: Nicholas P. Yensen, Tucson, Ariz.

[73] Assignee: Salt Weeds, (Partnership), Tucson, Ariz.

[21] Appl. No.: 797,988

[22] Filed: Nov. 26, 1991

Related U.S. Application Data

[63] Continuation-in-part of Ser. No. 398,262, Aug. 24, 1989.

[51] Int. Cl.[5] ..... A01H 5/00

[52] U.S. Cl. ..... Plt./100

[58] Field of Search ..... Plt. 88

[56] References Cited

PUBLICATIONS

Cluff et al (1983) Journal of Range Management 36(4) 419–422.

Somers, G. F. (1979) In the Biosaline Concept (Hollaender et al.) Plenum Press, N.Y., pp. 101–115.

Cunningham et al (1983) NTIS Bulletin #PB85-215010 New Mexico Water Resource Institute, NM State Univ.

*Primary Examiner*—James R. Feyrer

*Assistant Examiner*—E. F. McElwain

[57] ABSTRACT

A new and distinct variety, Yensen 4, of Distichlis sp., characterized by vigorous growth in salty soils, soft and palatable leaves and high yield.

1 Drawing Sheet

CROSS REFERENCE TO RELATED APPLICATION

This application is a continuation-in-part of my copending application entitled "*Distichlis spicata* var. Yensen 4A", assigned Ser. No. 07/398,262 and filed Aug. 24, 1989 and describing the same variety. With the exception of the continuation in part of the parent application, the parent application (Ser. No. 07/398,262) is now abandoned.

DESCRIPTION

The presently described plant is also described in a copending application for patent entitled "YENSEN 4a" a salt grass plant designated as *Distichlis spicata* variety Yensen 4A (=var. Yensen 4) and in commerce as ERAPL7 and NyPa (R) Forage, assigned to the present assignee and filed concurrently herewith on Aug. 24, 1989, and assigned Ser. No. 398,142.

The present invention relates to a new and distinct variety of a plant of the family Poaceae and particularly to a plant of the genus Distichlis sp., commonly known as salt grass, and is a perennial dioecious herbaceous flowering plant.

The accompanying drawing comprises a color photograph of my new variety of salt grass.

This new variety was discovered in a greenhouse at test plots of NyPa, Inc. (an Arizona corporation) in Tucson, Ariz.

Following some 14 years of study of salt tolerant plants, the new vareity was noted in a large collection of salt grass in a greenhouse in Tucson, Ariz. where approximately 2,300 salt grass plants (including varieties from around the world) were maintained. The greenhouse had been in use for a number of years to conduct hybridization and outcrossing work specifically to create new varieties with crop potential.

The new variety was compared with 40 other varieties of *Distichlis spicata* in Tucson. It was selected from the 40 other varieties to conduct a "large" field trial since it easily out performed the other varieties. The test field was a 0.4 acre plot located at the University of Arizona Maricopa Agricultural Center near Maricopa, Ariz. In this planting, single cuttings of the new variety were planted at one meter intervals. In four months the hay yield was 1600 pounds of sun dried hay, suggesting a hay yield of 2 tons per acre per cutting.

For descriptive purposes herein the yield may be characterized as high hay yield in providing a hay yield of 2 tons/acre/*four months*. The U.S. average alfalfa hay yield is approximately 2.39 tons/acre/year (USDA Ag. Statistics 1980, published by U.S. Government Printing Office) and yields may reach 11 tons/acre/*year* (Shery, R. W. 1972. *Plants for Man,* Prentice Hall, NJ, pg. 475). While it is not practical to plant acres of wild Distichlis varieties just of see what their hay yields would be, controlled studies have been conducted on small plots measuring above ground dry weight, as set forth below:

| STRAIN | EXTRAPOLATED HAY YIELD (Ton/Acre/4 Months) (mean ± standard error of the mean) |
|---|---|
| New Variety | 5.66 ± 1.42 |
| Wild varieties | |
| Hidalgo (Mexico) | 0.65 ± 0.16 |
| Coal (California) | 0.52 ± 0.13 |
| *D. palmeri* (Mexico) | 0.25 ± 0.05 |
| *D. palmeri* (Mexico) | 0.27 ± 0.08 |
| *D. palmeri* (Mexico) | 0.19 ± 0.05 |

These plants were grown under identical conditions which included daily irrigations and high nutrient solutions (Hoaglands) in semi-hydroponic systems. Such conditions are not normally found in agricultural fields and therefore the above table should be used for relative comparisons rather than trying to predict actual yields in large fields. The new variety had a significantly ($P<0.0001$) greater above ground dry weight yield (hay yield) than any of the wild varieties. As used herein "high hay yield" means at least 2.0 tons dry weight per acre in a four month period.

By way of definition palatable leaves (as used herein and discussed later) means that sheep, goats, calves and horses may consume the leaves as their sole source of nutrition for at least a two month period without any observed ill effects.

As used herein and discussed in detail later, soft, lax to mildly rigid, soft and tender, soft and palatable each means that leaf bending requires less than 1.25 grams (applied at 1 centimeter from the leaf collar) per millimeter width of leaf. This definition is very conservative in that actual measurements for the new variety were 0.73 g/mm of leaf with (3.17±0.34 g/4.9±0.1 mm) as compared to a Distichlis species (*Distichlis palmeri*) growing under virtually identical conditions and irrigation regime (water salinity measures 10,000 ppm) which required 1.39 g/mm of leaf width (5.51±0.50 g/3.5±0.1 mm) to induce bending.

One of the principal problems of potential forage crops for saline soil has been that the plants tend to accumulate salt in their tissues. The hay from the new variety had low salt levels in the stem and leaf tissues and is similar to alfalfa in this regard. Palatability studies have been conducted with goats, calves, cows, sheep and horses. All of them reaily ate hay of the new variety. Preference studies in Namibia (formerly South West Africa) were conducted with cows and sheep. Both the cows and sheep preferred the new variety to their regular feed (millet hay). Four calves and a horse were fed in Tucson, Ariz., on a diet of 100% of the new variety for a period of two months verifying its palatability at a practical level. As used herein, palatable leaves means that sheep, goats, calves and horses may consume the leaves as their sole source of nutrition for a period of two months without any observed ill effects.

Weight gain studies have not been done and no claims are made as to weight gain when consumed by animals, only with regard to its palatability. In comparison Lamson-Schribner (1900, *American Grasses I*, USDA Publisher, p. 273) describes *Distichlis spicata* as having, " . . . little agricultural value." " . . . although sometimes eaten by stock in the absence of better sorts . . . ", and [it] " . . . is considered a nuisance in farming lands . . . ".

The new variety has improved growth at salinities greater than 5,000 parts per million (ppm) salt and has optimal growth between 8,000 and 20,000 ppm salt (sea water is 35,000 ppm). converntional forage and hay crops have significantly reduced growth at salinities greater than 5,000 ppm and/or accumulate salts in their tissues making them unpalatable. The term "high salt tolerance" refers to the fact that the new variety has improved growth at salinities greater than, 5,000 ppm while conventional forage crops ahve reduced growth at salinities greater than 5,00ppm. It should be noted that other species and varieties of Distichlis also have high salt-toerance comparable to the new variety, but they do not have the functioal properties of the new variety. The optimal yields of the new variety with regard to fertilizer ansd watering rates are not known at this time. The new variety has first noted as different from other salt grasses for its vigorous growth in highly salty water and soft and tender leaves compared to thenormally stiff leaves.

The "vigorous growth" as used herein may be characterized as follows. The table below compares growth in terms of dry weight productivity (grams) of the new variety with five wild varieties of Distichlis, that were grown under the same conditions (which included five levels of salt from fresh water to near sea water and hence the high standard error of the mean). Also note that ash free dry weight was not determined because Distichlis, unlike many other halophytes, does not accumulate salt in the tissues. The five wild varieties selected for this study have typical growth rates observed in other wild varieties and, indeed, were selected for their "vigorous growth as used in the literature". And, compared to other grasses grown in the same salinities, these wild varieties could be said to have "vigorous growth as used in the literature". The dry weights represent entire plants (roots and shoots) grown from "same size" cuttings for four months. By comparison, it is very evident that the new variety is significiantly more "vigorous" than the wild varieties considered in the literature to be "vigorous".

| STRAIN | DRY WEIGHT (grams) (mean ± standard error of the mean) |
|---|---|
| New Variety | 1729.8 ± 356 |
| Hidalgo (Mexico) | 266.6 ± 59 |
| Coal (California) | 227.4 ± 57.1 |
| *D. palmeri* (Mexico) | 174.0 ± 57 |
| *D. palmeri* (Mexico) | 117.5 ± 30 |
| *D. palmeri* (Mexico) | 75.2 ± 20 |

Thus, vigorous growth, as used in the application, means that a 20 gram (dry weight) cutting will grow to greater than 500 grams (dry weight) in a four month period during the summer months under the climatic conditions of Tucson, Ariz. when irrigated with saline Hoaglands solution (10,000 ppm sodium chloride salt).

The softness of the leaves may be characterized as follows. The measurement and comparison of the bendability (softness) of leaves is not easily quantifiable and is not normally done. This said, the following study to measure the "resistance to bending" was conducted at a field site near Hermosillo, Sonora, Mexico where a grain variety (Yensen 3A) and the new variety are growing side by side under virtually identical conditions and irrigation regime (water salinity measures 10,000 ppm). Fresh, entire stems were taken to a windless site at the edge of the field. Stems were selected for similar maturity, full-sized and actively photosynthesizing and not yet entering senescence stages, i.e. the size and maturity that would normally be used for hay production.

Leaves 3, 4, 5 and 6 where lightly marked with a felt tip marker at a distance of 10 mm from the leaf collar (leaves 1 and 2 were not measured as their configuration on the stem tip requires that they remain voluted and not amenable to direct comparison). In order to use comparable portions of the leaves, only the first 10 mm of the leaf was used as leaf length of the two varieties is significantly different ($P<0.001$)—Yensen 3A, being shorter (45.5±0.5 mm) and very sharply pointed as is typical of Distichlis, while the leaves of the new variety are longer (93.1±5.9) and blunted.

Leaf measurements commenced with the 6th leaf and progressed up the stem so that measurement would not disturb unmeasured leaves. The leaf was held horizontal to place the bearing force at a right angle to the leaf. A double-looped, waxed thread (weighing 0.021 grams)-was slipped over the leaf and down to the 10 mm mark the waxed thread allowed an even distribution of weight across the leaf blade). Wire weights of 0.33 grams each were added to the lower loop until the leaf began "bending". Once a leaf had initiated "bending" no additional weight was necessary for the leaf to continue bending to a vertical position. The total weight necessary to initiate bending was recorded.

It should be noted that the new variety has significantly ($P<0.001$) wider leaves ($4.9\pm0.1$ mm) as compared to Yensen 3A ($3.5\pm0.1$ mm) implying that the new variety should have more resistance to bending.

The results, however, clearly demonstrate the opposite; that the "soft" leaves of the new variety actually have significantly ($P<0.001$) less resistance to bending (requiring only $3.17\pm0.34$ grams to induce bending) when compared to the thinner Yensen 3A leaves (which require $5.51\pm0.50$ grams to induce bending). Per millimeter of leaf width the new variety only required 0.73 grams to induce bending, whereas Yensen 3A required nearly twice this amount, i.e. 1.39 grams to induce bending.

As noted earlier and as used herein, soft, lax to mildly rigid, soft and tender, soft and palatable each means that leaf bending requires less than 1.25 grams (applied at 1 centimeter from the leaf collar) per millimeter width of leaf. This definition is very conservative in that actual measurements for the new variety were 0.73 g/mm of leaf width ($3.17\pm0.34$ g/$4.9\pm0.1$ mm) as compared to a Distichlis species (*Distichlis palmeri*) growing under virtually identical conditions and irrigation regime (water salinity measures 10,000 ppm) which requried 1.39g/mm of leaf width ($5.51\pm0.50$ g/$3.5\pm0.1$ mm) to induce bending.

The new variety can be reproduced via rhizomes, cuttings and stolons and is being so reproduced in test plots where other varieties are also being observed to determine the variation present.

The following is a detailed description of the new variety: Parentage: A vigorous shoot growing across the aforementioned greenhouse floor as an unknown outcross (or mutant) variety of Distichlis spp. Plant characteristics appear to be most closely aligned with those of *Distichlis spicata* although the wide leaves and robust form are not unlike *Distichlis palmeri*. The discovery of this new variety in the greenhouse and subsequent characterization followed the germination and planting and selection from literally millions of plants and seedling which included over 100 test plots, two greenhouses and a shade house in Tucson, Ariz. The particular greenhouse from which the new variety emerged had approximately 2,300 salt grass plants including varieties from various countries. Virtually all of these plants were subjected to various stresses; e.g. water stress, temperature stress, salt stress, etc. In some tests only 0.1% to 1.0% of the plants are allowed to survive to maturity. The ecotypic response of salt stress in Distichlis spp. phenotypes is a reduction in internode length and a stiffening of the blades and stem. While the new variety has this ecotypic response, the stiffening at high salt levels is markedly reduced. While the above may suggest a mutation parentage, it should be noted that there were other Distichlis phenotypes in the greenhouse with mildly reduced blade stiffness, albeit without the vigorous growth of the new variety.

Propagation: To date all rhizomes, shoots and tillers have held true to the distinguishing characteristics of the initial plant. Seed (caryopses) of the new variety have not been produced. The new variety, under the growing conditions of Tuscson, Ariz. are virtually free of inflorescences. In a $10\times10$ meter test plot in Tucson, three male inflorescences were found and were the first inflorescences known of the new variety.

Culms: Erect to procumbent when old; erect culms 30 to greater than 100 cm in height. New shoots are slightly succulent while old shoot are fibrous and tough. Procumbent culms frequently produce new shoots and roots at the nodes. Procumbent culms may become stolons of indeterminate length; 1 to 5 mm in diameter, glabrous. The color of the new variety is not significantly different from other varieties.

Rhizomes: Thick and scaled at nodes; pungent apex.

Blades: Lax to mildly rigid, pointed, involute (especially upon drying), distichous (0ccasionally moderately whorled), glabrous to slightly puberulent, 2 to 9 mm basal width, 30 to 50 veins at base, typically 50 to 150 mm in length.

Sheath: Glabrous to slightly puberulent with a tuft of wooly hairs at either side of the mouth; ligule smooth with a pubescent fringe.

Inflorescence (in the three known examples):

*Panicle.*—Erect, compoundly branched, 8 to 13 cm in length and extends beyond the leaves;

*Spikelet.*—With 11 to 20 flowers with subtending bracts infertile, 12 to 22 mm in length, 3 to 4 mm in width;

*Florets.*—Glumes broad, acute, keeled, 3–7 faint nerves; lemma is 5 to 6 mm in length, with the most distal on spikelet slightly shorter than the rest with a weak nerve running parallel and just lateral to a low keel, with a pair of nerves running longitudinally on both sides; palea is 5 to 6 mm in length, with the most distal on spikelet being slightly shorter than the rest;

*Anther.*—Typically 3 per floret, 2 to 3 mm in length, 0.3 to 0.5 mm in width, consisteing of two bilobate pollen sacks with midrib extending from approximately the first $\frac{1}{4}$ to the first $\frac{1}{2}$ of the anther length with the remainder (the basal portion) of the pollen sacks free, the ffree lobes more attenuated terminally than medially, filament attached to and continuous with "midrib".

*Pollen.*—15 to 30 microns in diameter, spherical, yellow.

The new variety has the following taxonomic and functional distinction over *Distichlis spicata* described in the following publications:

a) Lamson-Schribner, 1900, *American Grasses I*, USDA Publisher, p. 273:

Taxonomic distinctions

1) Lamson-Schribner describes the limits of the blade [leaf] width as 2–4 mm in width whereas the new variety has blades [leaves] typically twice this wide and up to 9 mm wide.

2) Lamson-Schribner describes the staminate spikelet length as being up to 18 mm, whereas the staminate spikelet length of the new variety is up to 22 mm.

3) Lamson-Schribner does not describe the panicle size of *Distichlis spicata*, whereas the new variety has panicles 8–13 cm in length.

4) Lamson-Schribner describes *Distichlis spicata* leaf texture as being "wiry". This is compared to the taxonomic description of the new variety which is "soft", "lax", and "tender".

Functional distinctions

Lamson-Schribner does not describe any functional distinctions of *Distichlis spicata* relevant to the species' value as animal food; specifically, growth rate, potential hay yield, degree of blade stiffness, or palatability, Lamson-Schribner does mention, however, that *Distichlis spicata* "*. . . is considered a nuisance in farming lands . . .*" and "*Although sometimes eaten by stock in the absence of better sorts, it has little agricultural value.*" *While in general terms this is clearly different from the new variety, Lamson-Schribner does not quantify the distinguishing characteristics. The inventor has quantified the above mentioned functional distinctions in order to distinguish the new variety from wild Distichlis varieties.* b) Gould, 1975, *The Grasses of Texas*, Texas A & M Press, pp. 372–373:

Taxonomic distinctions

1) Gould describes the blades [leaves] of*Distichlis spicata* as being 1–4 mm in width, whereas the blades of the new variety are 2–9 mm in width.

2) Gould describes the spikelet length as being typically up to 18 mm with unusual spikelets up to 28 mm. The Staminate spikelet length of the new variety is up to 22 mm suggesting the new vareity spikelet length is unusual.

3) Gould limits the panicle size of *Distichlis spicata* at 8 cm in length, whereas the new variety has panicles 8–13 cm in length.

4) Gould taxonomically describes *Distichlis spicata* leaf texture as being "thick, firm". This is compared to the taxonomic description of the new variety which is "soft", "lax", and "tender".

Functional distinctions

Gould does not describe any functional distinctions of *Distichlis spicata* relevant to the species' value as animal food; specifically, growth rate, potential hay yield, degree of blade stiffness, or palatability. The inventor has quantified these functional distinctions in order to distinguish the new vareity from wild Distichlis varieties.

c) Fernald, 1950, *Gray's Manual of Botany*, American Book Company, p. 231.

Taxonomic distinctions

1) Fernald does not describe the blade [leaf] width of *Distichlis spicata.*

2) Fernald does not describe the spikelet length.

3) Fernald limits the panicle size of *Distichlis spicata* at 8 cm in length, whereas the new variety has panicles 8–13 cm in length.

4) Fernald describes all Distichlis leaf texture as being "rigid". This is compared to the taxonomic description of the new vareity which is "soft", "lax", and "tender".

Functional distinctions

Fernald's only description of any functional distinctions, with regard to *Distichlis spicata* as an animal food, is that the plants are "rigid". Fernald does not describe any other functional distinctions of *Distichlis spicata* relevant to the species' value as animal food; specifically, growth rate, potential hay yield, degree of blade stiffness, or palatability. The inventor has quantified these functional distinctions in order to distinguish the new vareity from wild Distichlis varieties.

The new vareity has the following taxonomic and functional distinctions over *Distichlis stricta* described in the following publications:

a) Shreve et al., 1964, *Vegetation and Flora of the Sonoran Desert I*, Stanford Press, P. 246:

Taxonomic distinctions

1) Shreve et al. describes the limits of the blade [leaf] widh as 2–4 mm in width whereas the new variety had blades [leaves] typically twice this wide and up to 9 mm wide.

2) Shreve et al. describes the staminate spikelet length as being 8–15 mm, whereas the staminate spikelet length of the new vareity is 12–22 mm.

3) Shreve et al. describe the panicle size of *Distichlis stricta* as being 2–6 cm in length, whereas the new variety has panicles 8–13 cm in length.

4) Shreve et al. does not describe *Distichlis stricta* leaf texture.

5) Shreve et al. describes *Distichlis stricta* as having culms "commonly 10–30 cm, or sometimes 60 cum tall", whereas the new variety commonly has culms well over 30 cm tall and not uncommonly over 100 cm.

6) Shreve et al. describes *Distichlis stricta* as having spikelets with 5–12 flowers, whereas the new variety has 12–22 flowers.

7) Shreve et al. describes the blades a 3–9 cm long, whereas the new variety has blades 5-15 cm long.

Functional distinctions

Shreve does not describe any functional distinctions of *Distichlis stricta* relevant to the species' value as animal food; specifically, growth rate, potential hay yield, degree of blade stiffness, or palatability. The inventor has quantified these functional distinctions in order to distinguish the new vareity from wild Distichlis varieties.

b) Fernald, 1950, *Gray's Manual of Botany*, American Book Company, p. 231:

Taxonomic distinctions

1) Fernald does not describe the blade [leaf] width of *Distichlis stricta.*

2) Fernald does not describe the spikelet length.

3) Fernald describes the panicle size of *Distichlis spicata* as 2–8 cm in length, whereas the new variety has panicles 8–13 cm in length.

4) Fernald describes all Distichlis leaf texture as being "rigid". This is compared to the taxonomic description of the new vareity which is "soft", "lax", and "tender".

Functional distinctions

Fernald's only description of any functional distinctions, with regard to *Distichlis stricta* as an animal food, is that the plants have leaves with "sharp tips." Fernald does not describe any other functional distinctions of *Distichlis stricta* relevant to the species' value as animal food; specifically, growth rate, potential hay yield, degree of blade stiffness, or palatability. The inventor has quantified these functional distinctions in order to distinguish the new variety from wild Distichlis varieties.

In summary the botanical/taxonomic characteristics of the new vareity, which most easily distinguish the new vareity from all other Distichlis species and/or varieties, are its having one or more of the following:

a) stems which can be 0.4 or more cm in diameter,
b) stems which can be 1.2 or more meters high,
c) leaf bases which can be 0.8 or more cm at base, or
d) a leaf base vain number which can be 50 or more.

I claim:

1. A new and distinct variety of *Distichlis spicata* as shown and described, which is principally characterized by high hay yield and soft palatable leaves.

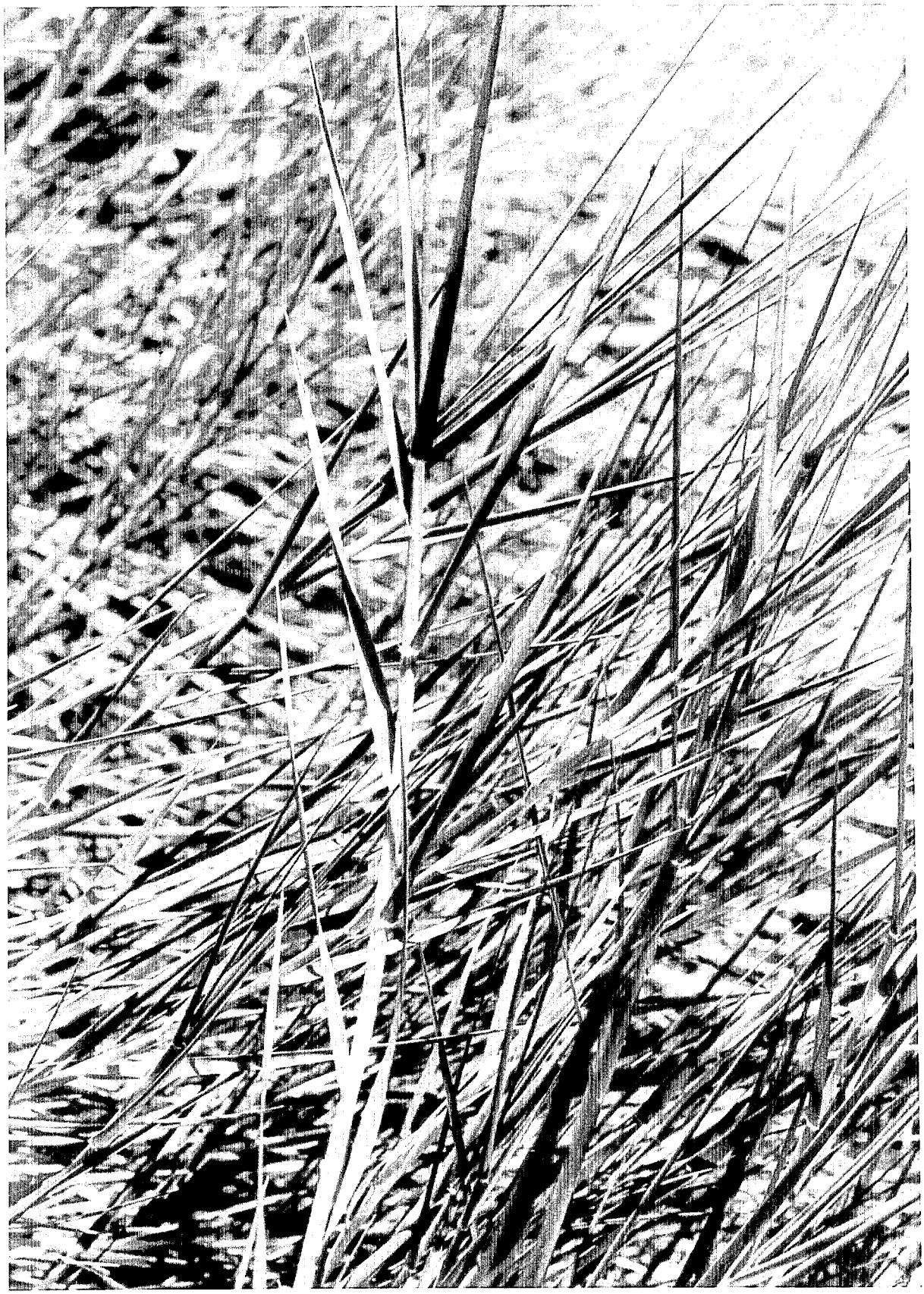

* * * * *